United States Patent
Zhao et al.

(10) Patent No.: US 11,896,351 B2
(45) Date of Patent: Feb. 13, 2024

(54) MICROBENDING FIBER-OPTIC SENSOR FOR VITAL SIGN MONITORING AND CO-EXTRACTION OF RESPIRATION AND HEARTRATE

(71) Applicant: Hong Kong Applied Science and Technology Research Institute Company, Limited, Hong Kong (HK)

(72) Inventors: Qian Cheng Zhao, Hong Kong (HK); Tsz Chung Leung, Hong Kong (HK); Man Sang Kwok, Hong Kong (HK)

(73) Assignee: Hong Kong Applied Science and Technology Research Institute Company Limited, Hong Kong (HK)

( * ) Notice: Subject to any disclaimer, the term of this patent is extended or adjusted under 35 U.S.C. 154(b) by 660 days.

(21) Appl. No.: 17/083,478

(22) Filed: Oct. 29, 2020

(65) Prior Publication Data

US 2022/0133154 A1 May 5, 2022

(51) Int. Cl.
*A61B 5/0205* (2006.01)
*A61B 5/11* (2006.01)
(Continued)

(52) U.S. Cl.
CPC .......... *A61B 5/0205* (2013.01); *A61B 5/1102* (2013.01); *A61B 5/113* (2013.01);
(Continued)

(58) Field of Classification Search
CPC ..... A61B 5/0205; A61B 5/6892; G01L 1/245; G02B 6/4202; G02B 6/4298
See application file for complete search history.

(56) References Cited

U.S. PATENT DOCUMENTS 6,498,652 B1 12/2002 Varshneya et al.
9,414,786 B1 8/2016 Brockway et al.
(Continued)

FOREIGN PATENT DOCUMENTS

CN 104269026 B 1/2017
CN 107072565 A 8/2017
(Continued)

OTHER PUBLICATIONS

FOA Guide; "Optical Fiber"; The FOA Reference Guide to Fiber Optics; 1999-2018.*
(Continued)

*Primary Examiner* — Dixomara Vargas
(74) *Attorney, Agent, or Firm* — Stuart T. Auvinen; gPatent LLC

(57) ABSTRACT

A fiber-optic sensor matt detects movements of a person on the matt that cause microbending of a fiber-optic cable that is arranged into a symmetric pair of radial ring groups within the matt. There are no cross-over points or overlapping of the fiber-optic cable within the symmetric pair of radial ring groups that could cause fiber wear and noisy readings. Microbending of the fiber-optic cable pressed into a mesh modulates the light intensity received, which is analyzed to extract both respiration and heart BallistoCardioGram (BCG) waveforms by convolution with Daubechies dB5 wavelet and scaling functions. The reconstructed level-4 detail waveform is output as the extracted BCG, while the reconstructed level-6 approximation waveform is output as the extracted respiration waveform. Respiration and heart rates and variations can be generated from the extracted waveforms. An integrated Fast Wavelet Transform (FWT) using dB5 wavelet thus generates both respiration rate and heart rate.

16 Claims, 14 Drawing Sheets

(51) Int. Cl.
  *A61B 5/113* (2006.01)
  *A61B 5/00* (2006.01)
  *G02B 6/42* (2006.01)
  *G01L 1/24* (2006.01)
  *A61B 5/024* (2006.01)
  *A61B 5/08* (2006.01)

(52) U.S. Cl.
  CPC .......... *A61B 5/1126* (2013.01); *A61B 5/6892* (2013.01); *A61B 5/726* (2013.01); *G01L 1/245* (2013.01); *G02B 6/4202* (2013.01); *G02B 6/4298* (2013.01); *A61B 5/02444* (2013.01); *A61B 5/0816* (2013.01); *A61B 2562/0233* (2013.01)

(56) References Cited

U.S. PATENT DOCUMENTS

| | | | |
|---|---|---|---|
| 9,655,526 | B2 | 5/2017 | Hu |
| 10,555,691 | B2* | 2/2020 | Chen .................... A61B 5/447 |
| 10,750,981 | B2* | 8/2020 | Newberry ............. A61B 5/1118 |
| 2011/0302694 | A1* | 12/2011 | Wang ................... A61B 5/6806 2/160 |
| 2012/0123232 | A1* | 5/2012 | Najarian ................. G16Z 99/00 600/407 |
| 2012/0203117 | A1* | 8/2012 | Chen ..................... A61B 5/7214 600/595 |
| 2016/0089031 | A1* | 3/2016 | Hu ........................ A61B 5/1116 600/479 |
| 2016/0338601 | A1 | 11/2016 | Yang |
| 2017/0071550 | A1* | 3/2017 | Newberry ............. A61B 5/4845 |
| 2017/0215736 | A1 | 8/2017 | Hu |
| 2018/0160947 | A1 | 6/2018 | Hu |
| 2018/0214026 | A1* | 8/2018 | Goodall ............... A61B 5/1079 |
| 2018/0214066 | A1* | 8/2018 | Goodall ............... A61B 5/1077 |
| 2019/0134308 | A1* | 5/2019 | Newberry .............. A61B 5/412 |

FOREIGN PATENT DOCUMENTS

| | | |
|---|---|---|
| CN | 110448282 A | 11/2019 |
| CN | 110558956 A | 12/2019 |
| CN | 110974198 A | 4/2020 |
| CN | 111343902 A | 6/2020 |
| WO | WO2015112095 A | 7/2015 |

OTHER PUBLICATIONS

Hong-Zhong et al.; "Wavelet-Based Data Processing for Distributed Fiber Optic Sensors", Proceedings of the Fifth International Conference on Machine Learning and Cybernetics, Dalian, Aug. 13-16, 2006.*

Allan et al.; "Applications of Discrete Wavelet Transform in Optical Fibre Sensing"; Discrete Wavelet Transforms; 2011.*

Ibrahim Sadek; "Heart Rate Detection using a Contactless Bed Sensor: A Comparative Study of Wavelet Methods"; pp. 1-4; (2021).*

Zhihao Chen et al.; "Simultaneous measurement of breathing rate and heart rate using a microbend multimode fiber optic sensor"; Journal of Biomedical Optics vol. 19(5); pp. 1-11, 2014.*

Rene Jaros et al.; "Fiber-Optic Interferometry-Based Heart Rate Monitoring"; Transactions on Instrumentation and Measurement, vol. 71, 2022.*

Changyuan Yu et al.; "Non-invasive smart health monitoring system based on optical fiber interferometers"; 2017 16th International Conference on Optical Communications and Networks (ICOCN).*

Shaopeng Liu et al.; "Tissue Artifact Removal from Respiratory Signals Based on Empirical Mode Decomposition"; Annals of Biomedical Engineering, vol. 41, No. 5, May 2013 ( 2013) pp. 1003-1015.*

ISR and Written Opinion, PCT/CN2020/126702, Jul. 26, 2021.

Raaed Faleh Hassan and S. Shaker, "ECG Signal De-Noising and Feature Extraction using Discrete Wavelet Transform." International Journal of Engineering Trends and Technology vol. 63 No. 1, pp. 32-39, Sep. 2018.

Kim et al., "Ballistocardiogram: Mechanism and Potential for Unobtrusive Cardiovascular Health Monitoring", Nature Sci. Rep. 6, 31297; doi: 10.1038/srep31297 (2016), Aug. 2016.

Lagakos et al., "Microbend fiber-optic sensor", Applied Optics, vol. 26 No. 11, Jun. 1987.

Paul, S., A. Sinha, S. Roy and S. Kundu, "Feature Extraction from an ECG Signal of Various Cardiac Patients Using Daubechies Decomposition Technique", IJSR vol. 8, No. 4, Apr. 2020.

Patil, G. M., K. S. Rao and K. Satyanarayana, "Heart Disease Classification Using Discrete Wavelet Transform Coefficients of Isolated Beats", Springer Berlin Heidelberg, ICBME 2008, Proceedings 23, pp. 60-64, 2009.

* cited by examiner

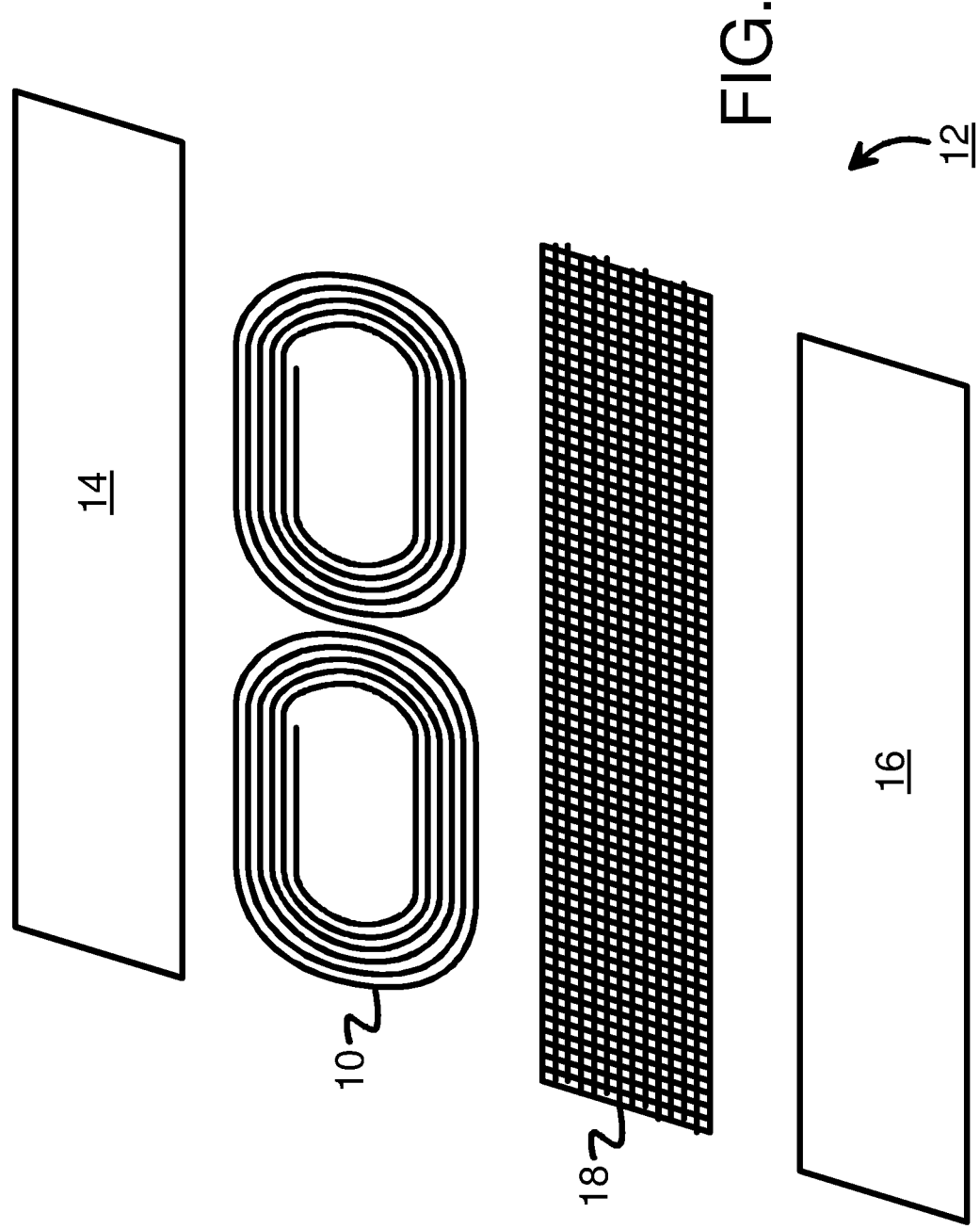

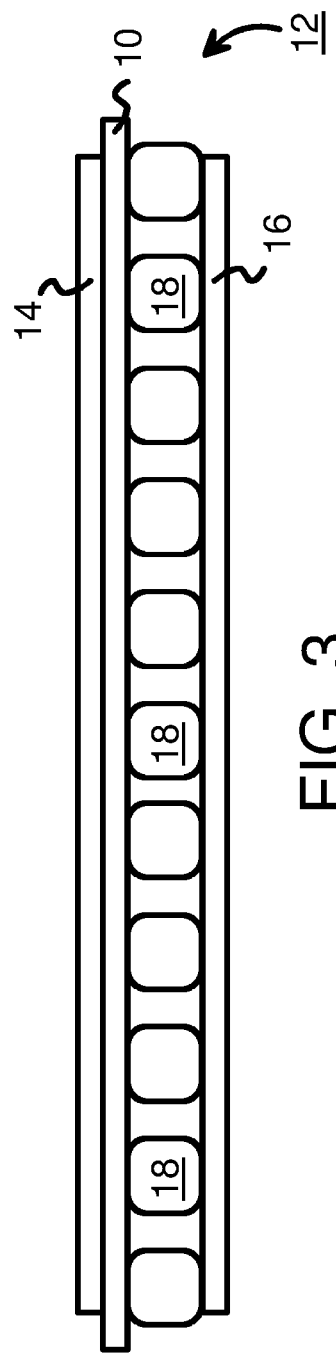
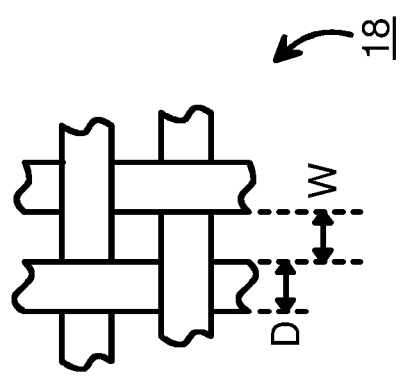
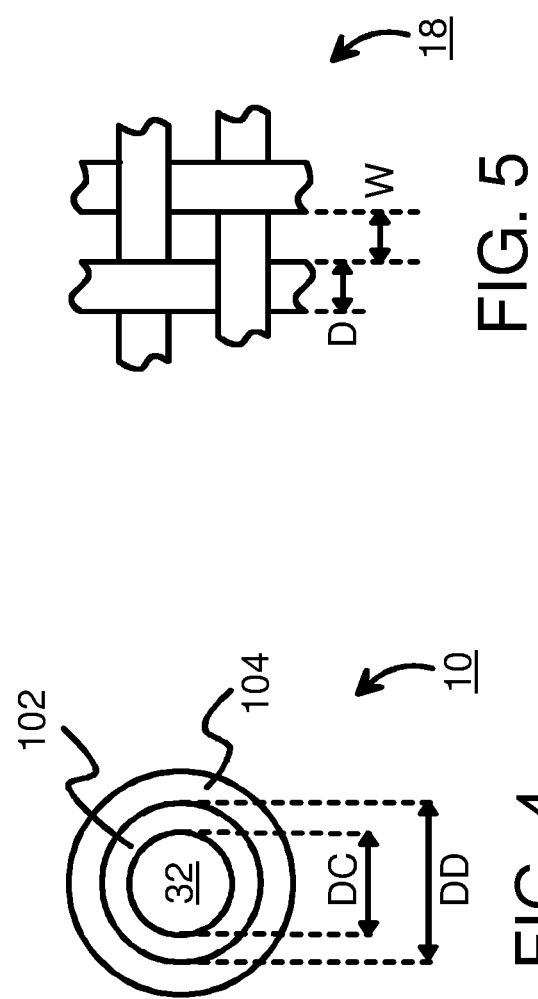

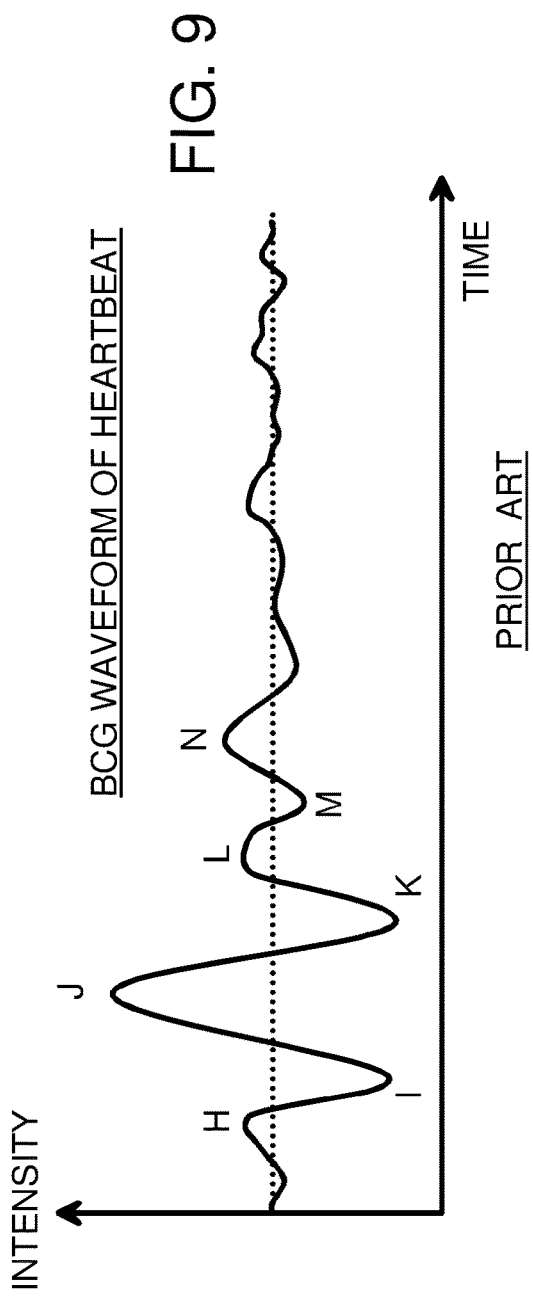
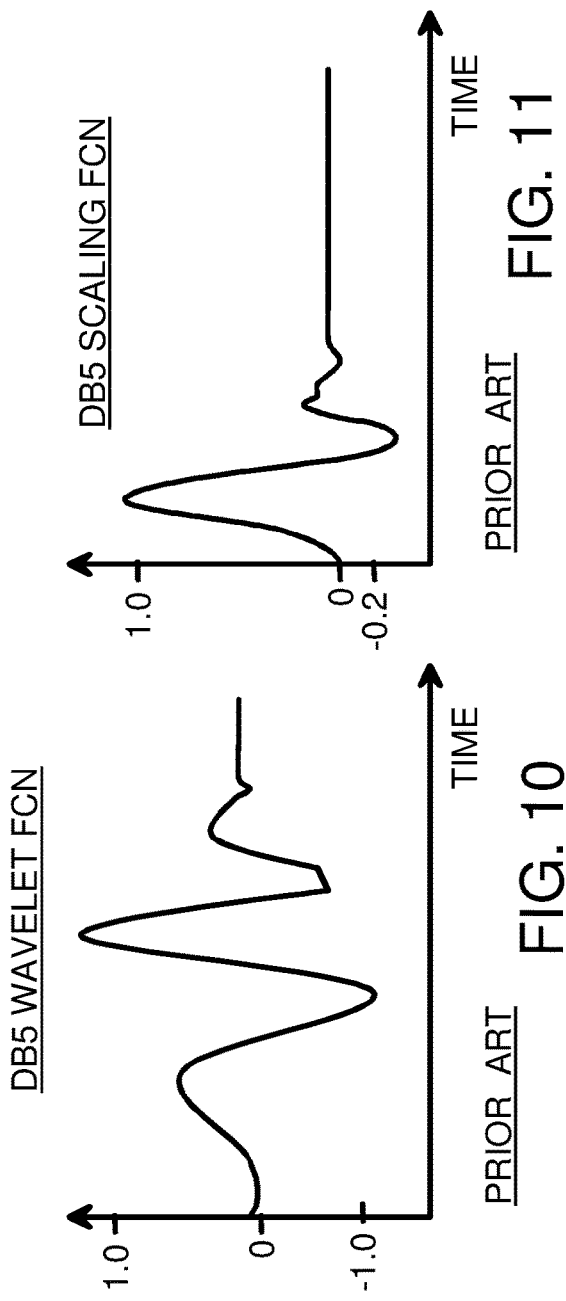

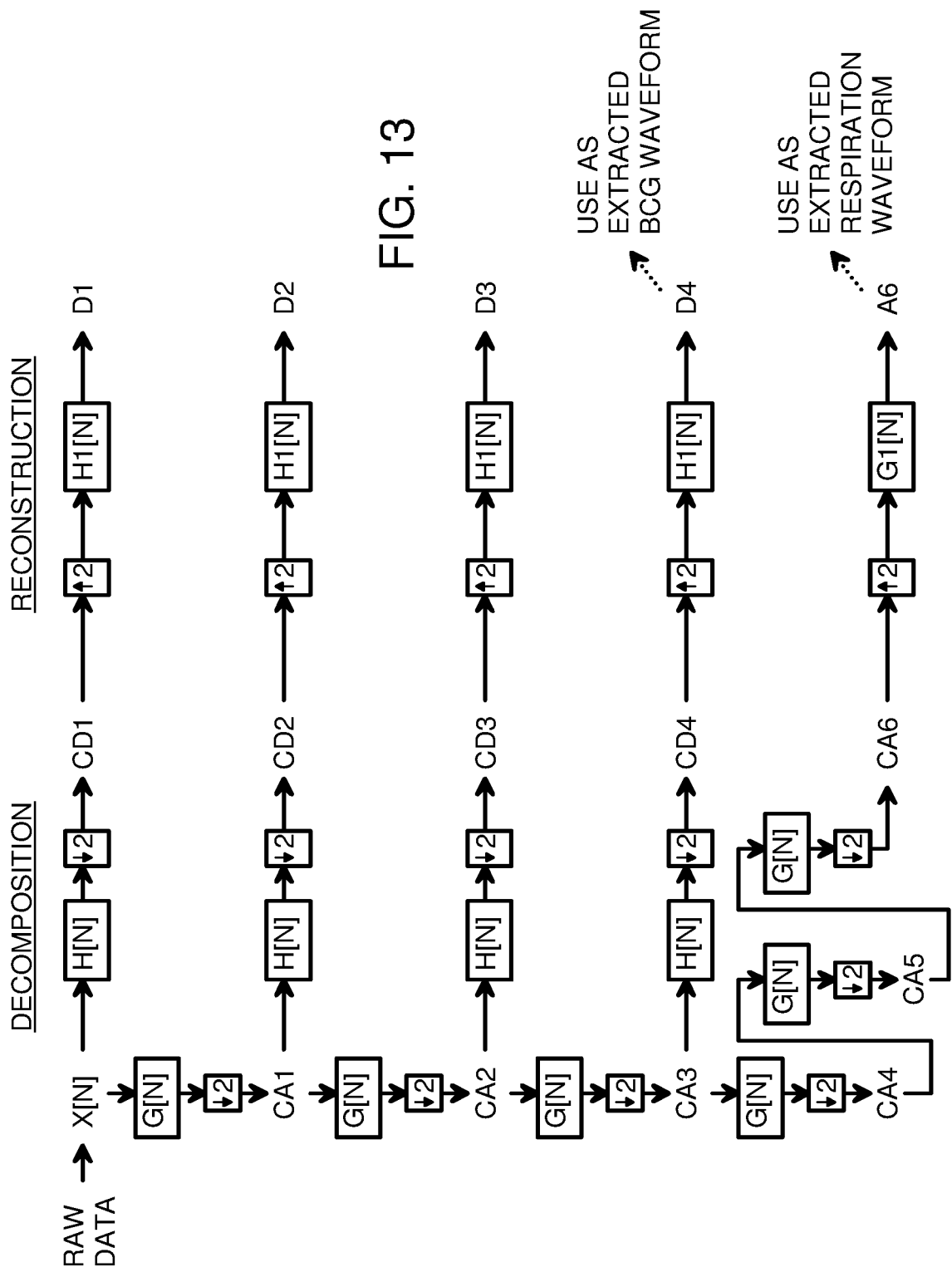

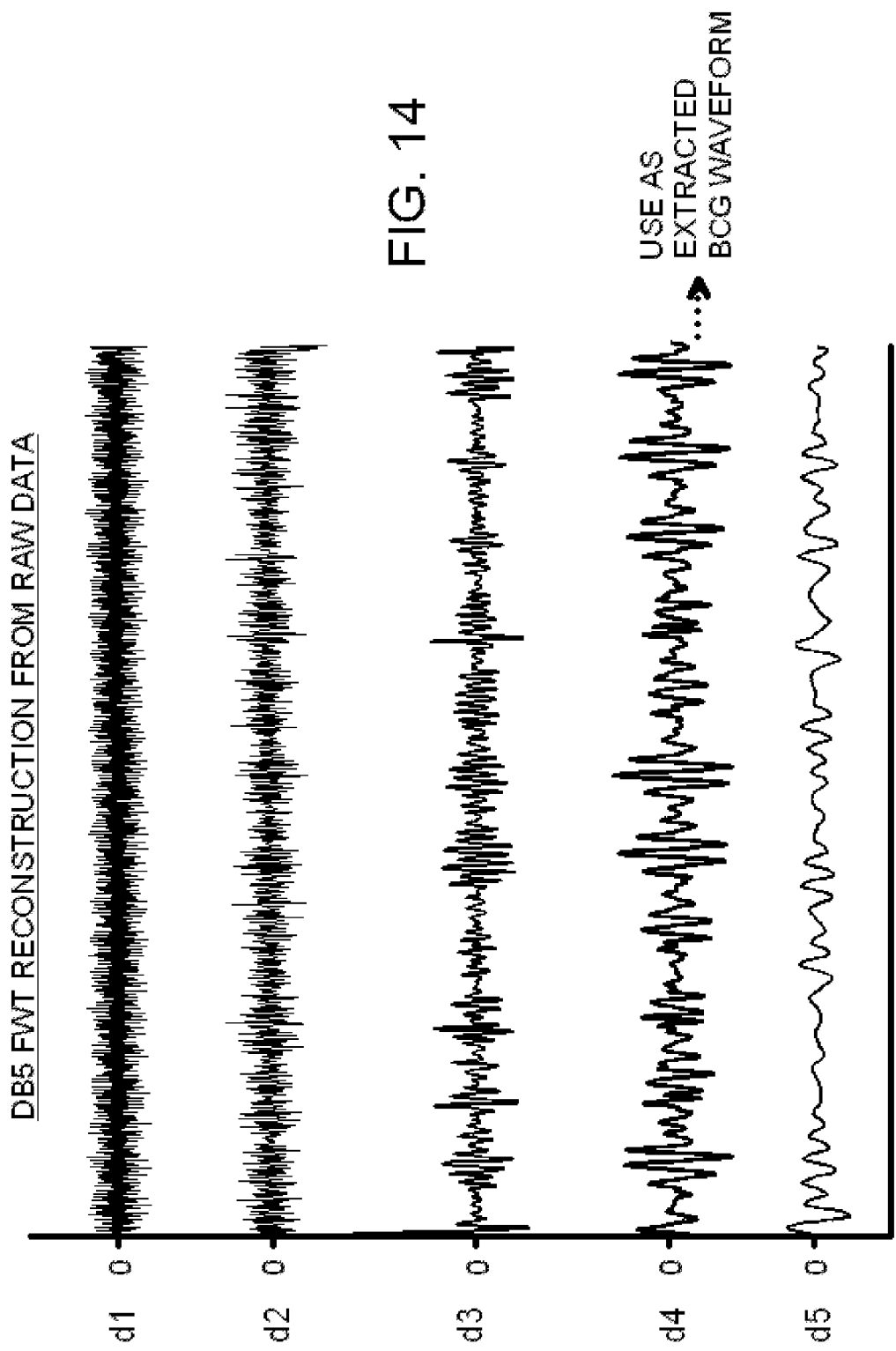

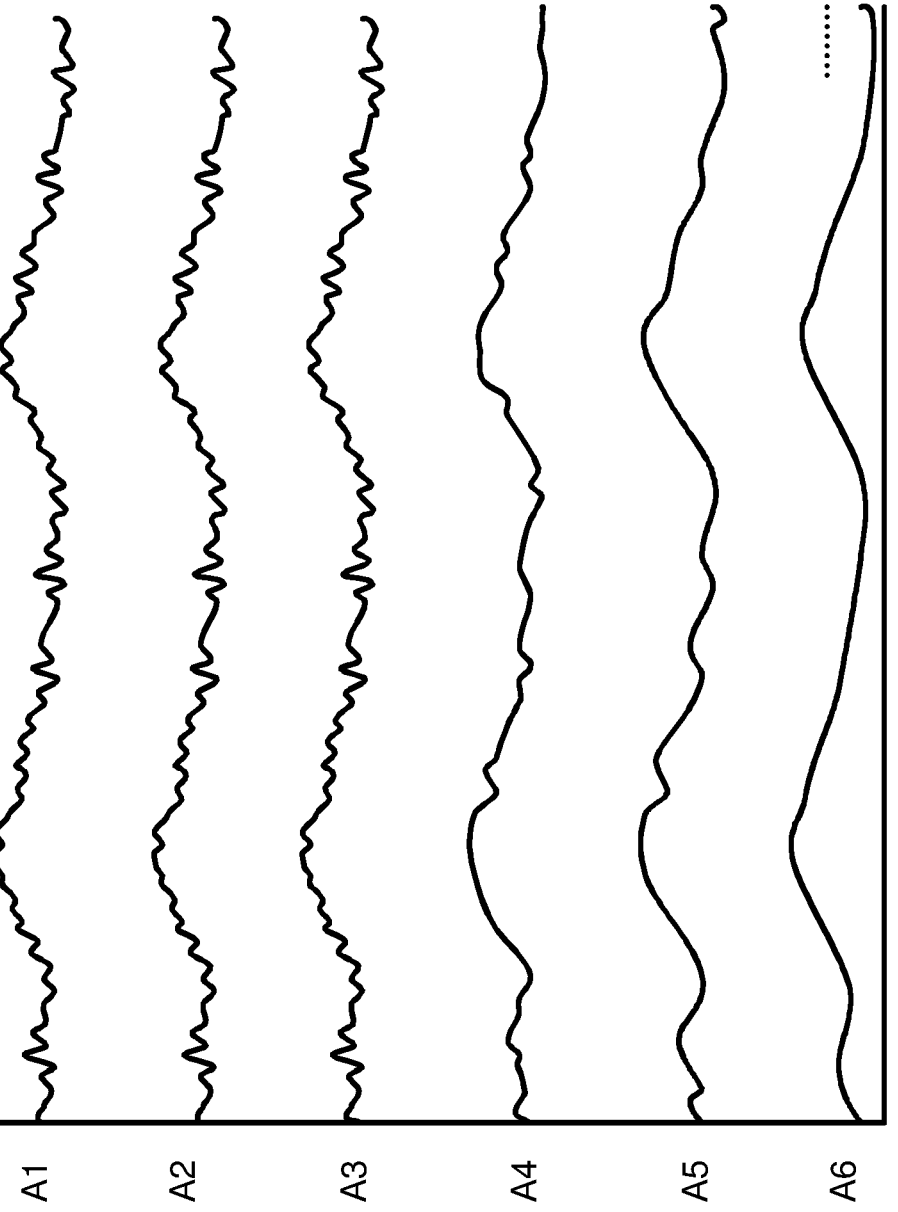

MICROBENDING FIBER-OPTIC SENSOR FOR VITAL SIGN MONITORING AND CO-EXTRACTION OF RESPIRATION AND HEARTRATE

FIELD OF THE INVENTION

This invention relates to fiber-optic sensors, and more particularly to extraction of respiration and heart rate from a microbending fiber-optic matt.

BACKGROUND OF THE INVENTION

Vital sign measurements such as heart rate have traditionally been performed by electrodes attached to a patient's chest. More recently, fiber-optic matts have been placed underneath a patient, allowing the patient's respiration rate to be determined by the bending of light in the optical fibers in the matt as the patient slowly rocks back and forth due to his breathing.

Interferometers and coherent light sources such as lasers have been used for fiber-optic matts, but lasers and interferometers can add expense and complexity. Such sensitive equipment may be sensitive to temperature and require frequent re-calibration.

With the proper selection of fiber diameters and mesh geometry, microbending can be used rather than macrobending. Microbending can eliminate complex optics such as interferometers, but it can be sensitive to misalignment with the mesh layer that deforms the fiber optic cable. Such misalignment can add noise and unreliability.

The pattern of the fiber optic cable can reduce misalignment sensitivity. For example, a serpentine pattern or many loops may reduce misalignment sensitivity. However, such loops may result in cross points, where the fiber cable crosses over itself where the loop is closed. These cross points are undesirable, since they can wear and damage the fiber with repeated matt movements as the fibers repeatedly rub on each other.

To improve sensitivity, many loops may be required to increase the density of the fiber loops within the matt. Pressure points occur where the fibers cross at the cross points. So there may be many such cross points in a matt, increasing the likelihood of fiber wear or failure. These cross-points may also introduce noise into the measure signals, caused by the non-uniform stress at these cross-points. Spikes, discontinuities, and non-linearity may be introduced into the measurement signals from a matt with many cross-points.

It would be desirable to use a fiber-optic matt to measure both heartbeat and respiration rates. Complex signal processing such as FIR filters and conversion from the time domain to the frequency domain have been used to separate heart and respiration signals. Interferometers or coherent laser light may also be used to extract both heart and respiration rates from a single fiber-optic matt.

What is desired is a fiber-optic matt that reduces the number of cross points while still having a high fiber density. It is desired to use non-coherent light in the fibers, without complex optics such as for an interferometer. It is further desired to extract both respiration and heart rate from the light signals modulated by the matt. It is desired to extract both heart rate and respiration rate using similar Fast Wavelet Transform (FWT) functions in the time domain.

BRIEF DESCRIPTION OF THE DRAWINGS

FIG. 2 shows the components of the sensor matt in more detail.

FIG. 3 is a cross-sectional diagram of the sensor matt.

FIG. 4 is a cross-sectional diagram of the fiber-optic cable.

FIG. 5 is a close-up top view of a portion of the mesh layer.

FIG. 9 shows a prior-art BCG waveform of a single heart beat.

FIG. 10 shows the prior-art Daubechies dB5 wavelet function.

FIG. 11 shows the prior-art Daubechies dB5 scaling function.

FIG. 13 is a diagram illustrating an integrated Daubechies wavelet process to reconstruct both respiration and BCG waveforms.

FIG. 14 shows reconstructed detail waveforms generated by the integrated FWT process of FIG. 13.

FIG. 15 shows reconstructed approximation waveforms generated by the integrated FWT process of FIG. 13.

DETAILED DESCRIPTION

The present invention relates to an improvement in fiber-optic health monitors. The following description is presented to enable one of ordinary skill in the art to make and use the invention as provided in the context of a particular application and its requirements. Various modifications to the preferred embodiment will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 1:
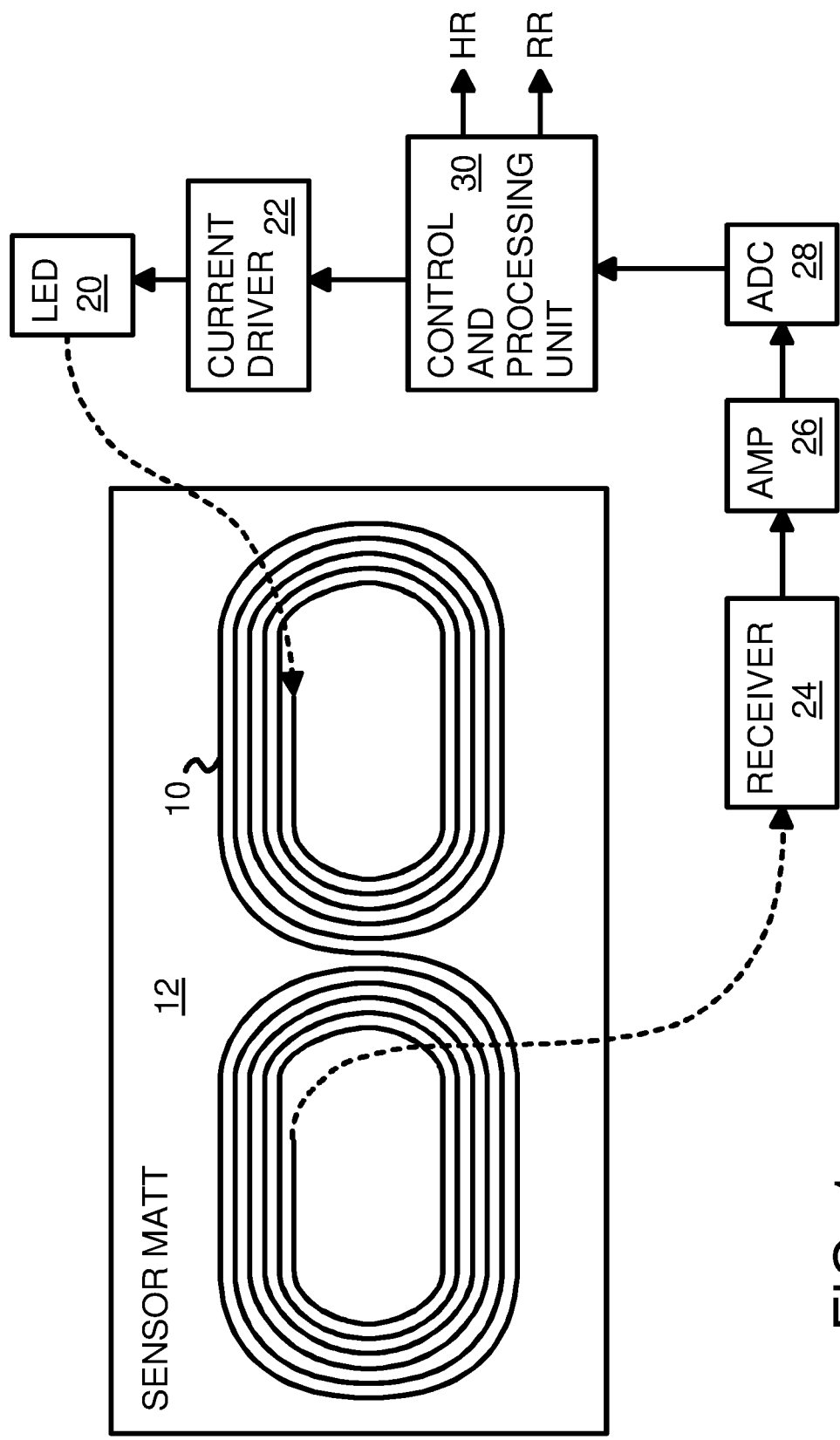
FIG. 1 is a simplified diagram of a fiber-optic sensor of heart and respiration rates.

FIG. 1 is a simplified diagram of a fiber-optic sensor of heart and respiration rates. Light-Emitting Diodes (LED) 20 is a non-coherent light source with an intensity set by current driver 22. The light intensity could be fixed, or the light intensity could be periodically adjusted, such as by control and processing unit 30. For example, control and processing unit 30 could monitor the sensor output over a time period and then adjust current driver 22 to adjust an average output to be near the mid-point of the sensor range.

The light from LED 20 is carried by fiber-optic cable 10 in sensor matt 12. Fiber-optic cable 10 is arranged to form a symmetric pair of radial ring groups in sensor matt 12. Fiber-optic cable 10 is circled smoothly from the inside of one ring to the outside of the other ring without any intersecting or overlapping. Thus cross-points are eliminated by the arrangement of the symmetric pair of radial ring groups.

The leader part of fiber-optic cable 10 that connects LED 20 to the inside of the right radial ring in sensor matt 12, and the exit portion of fiber-optic cable 10 that connects the inside of the left radial ring in sensor matt 12 to receiver 24, can be out of the plane of sensor matt 12, or can have additional padding to prevent wear from rubbing. There are very few cross-points for the leader and exit cables, however, the main body of the sensor has no cross points and thus is stable for sensing of microbending.

The light coming out of the exit portion of fiber-optic cable 10 is sensed by an optical sensor in receiver 24. Receiver 24 senses the intensity of the received light. The received light intensity is modulated by bending of fiber-optic cable 10 within sensor matt 12 as the patient lying on sensor matt 12 moves. Small motions such as from his breathing or from his heart beating may be detected by receiver 24.

Amplifier 26 amplified the signal detected by receiver 24, and Analog-to-Digital Converter (ADC) 28 converts the amplified analog signal to a series of digital values. These digital values are processed by control and processing unit 30 to extract both the heart rate HR and the respiration rate RR.

FIG. 2 shows the components of the sensor matt in more detail. Sensor matt 12 has four layers attached together. Fiber-optic cable 10 is arranged into a symmetric pair of radial ring groups that fall within a plane or layer within sensor matt 12. Mesh 18 have openings that are similar in size to the diameter of fiber-optic cable 10. Top cover 14 and bottom layer 16 sandwich mesh 18 and fiber-optic cable 10 together within sensor matt 12. Top cover 14 and bottom layer 16 are made from a non-rigid material so that they may flex and apply varying pressure gradients to fiber-optic cable 10 as a person laying on top cover 14 moves and breathes.

FIG. 3 is a cross-sectional diagram of the sensor matt. Sensor matt 12 has top cover 14 and bottom layer 16 pressing fiber-optic cable 10 against mesh 18. When a person lays on top of sensor matt 12, his body weight puts pressure on top cover 14 that presses portions of fiber-optic cable 10 into the spaces or opening in mesh 18. Fiber-optic cable 10 bends into these openings in mesh 18, causing the light passing through fiber-optic cable 10 to be attenuated. This attenuation of light varies as the person breaths and his heart beats because of shifts in the person's pressure on sensor matt 12.

FIG. 4 is a cross-sectional diagram of the fiber-optic cable. Fiber-optic cable 10 has core 32 that light passes through, cladding 102 that reflects light back into core 32, and coating layer 104 that protects the cable. Core 32 has a diameter DC, while DD is the larger diameter including cladding 102 around core 32. Core 32 diameter DC is greater than 50% of diameter DD that also includes cladding 102. Fiber-optic cable 10 is a multi-mode optical fiber.

FIG. 5 is a close-up top view of a portion of the mesh layer. Mesh 18 has strands weaved or intertwined together to form openings. The width of the strands is D while the openings have a width of W.

Mesh 18 acts as a deformer structure. When pressure is applied to top cover 14, this pressure is transferred to fiber-optic cable 10. First portions of fiber-optic cable 10 bend into openings in mesh 18, while second portions of fiber-optic cable 10 flexes against mesh 18.

Macrobending occurs when the width opening W is much larger than the fiber-optic diameter DD. Relatively large and sharp bends in fiber-optic cable 10 can occur since the fiber fits into the large openings.

Microbending occurs when the width opening W is about the same size as the fiber-optic diameter DD. Relatively small bends in fiber-optic cable 10 occur since the fiber cannot bend fully into the small openings. Instead, the fiber bends slightly over the openings. These smaller bends with microbending are more desirable since less noise and discontinuities are introduced into the fiber.

Microbending occurs when the surface area of the openings is between 30% and 60% of the total surface area of the mesh. The ratio for W and DD is around 0.5 to 0.6 so that microbending occurs.

Figure 6:
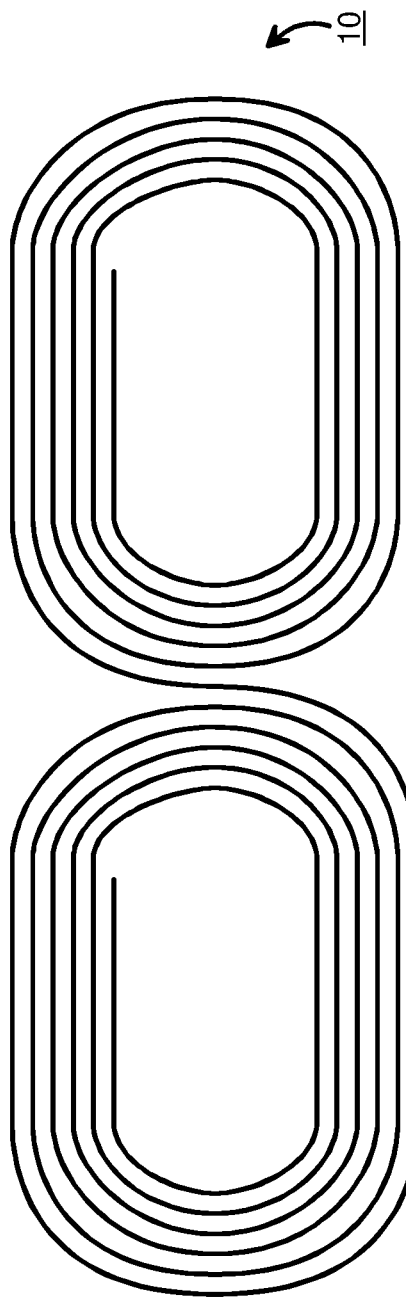
FIG. 6 shows a symmetric pair of radial ring groups of the fiber.

FIG. 6 shows a symmetric pair of radial ring groups of the fiber. Fiber-optic cable 10 is arranged into two groups of radial rings. The right group and the left group are jointed together at the outside of the ring groups by the outer fiber ring. Fiber-optic cable 10 continues out of the plane of the symmetric pair of radial ring groups at the end of the inner rings. At these points fiber-optic cable 10 bends upward or downward, out of the plane of the symmetric pair of radial ring groups, or become the leader cable or the exit cable portions of fiber-optic cable 10 that connect to the LED light source or receiver.

Figure 7:
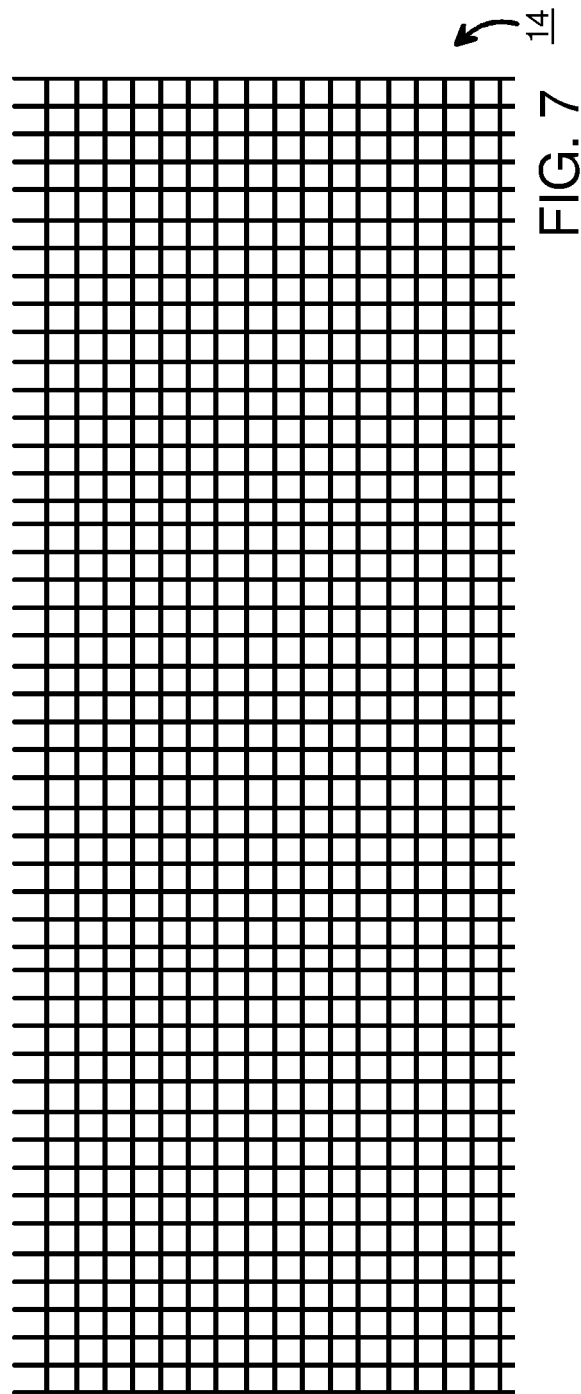
FIG. 7 shows the mesh in more detail.

FIG. 7 shows the mesh in more detail. FIGS. 6 and 7 are drawn at the same scale. Mesh 14 has openings that are slightly larger than the diameter of fiber-optic cable 10, and the ring-to-ring pitch of the fiber rings is slightly smaller than the pitch of mesh 14. This relationship of W and D allows the fibers to bend slightly into the openings of mesh 14 without sharp bends occurring in the fiber.

Figure 8:
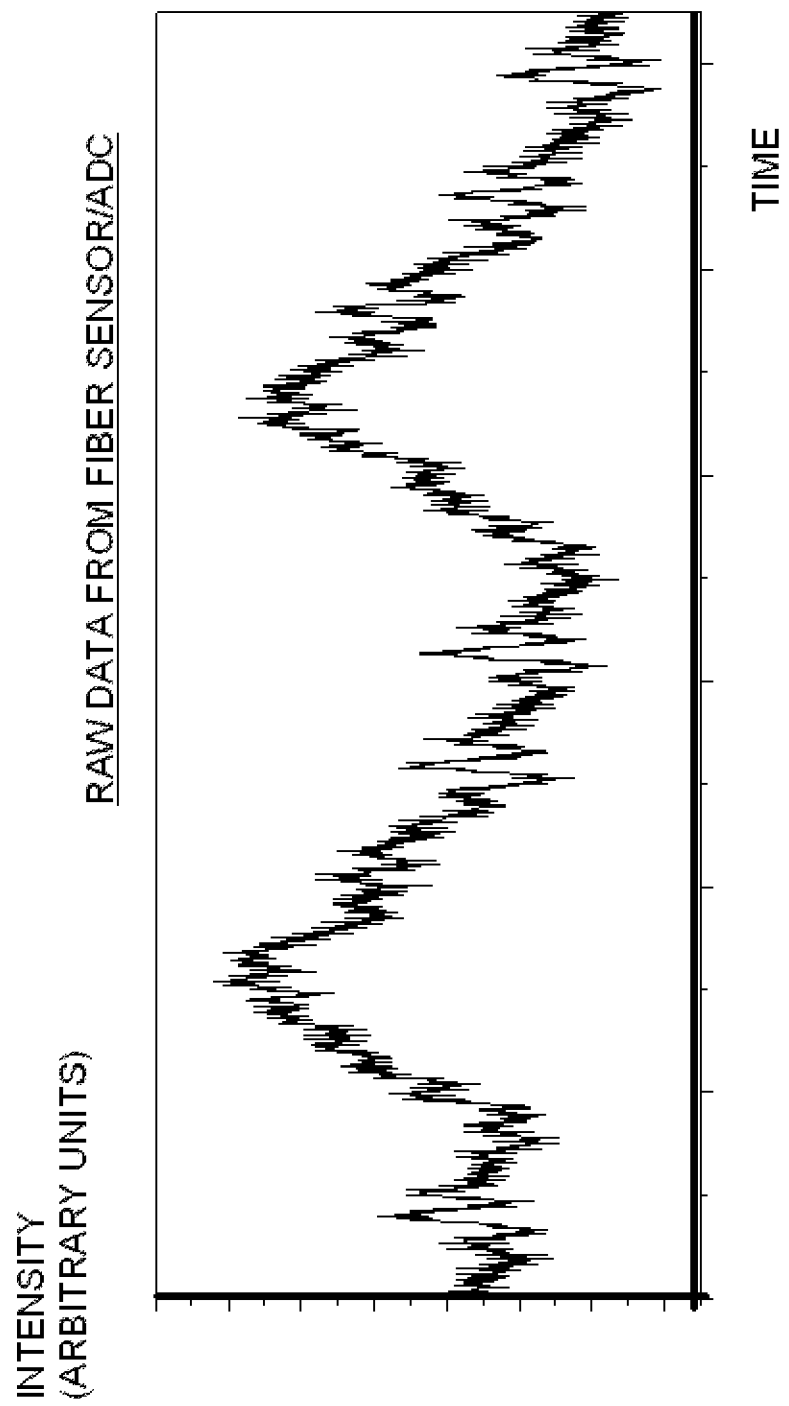
FIG. 8 is a plot of the raw data from the optic receiver.

FIG. 8 is a plot of the raw data from the optic receiver. The light passing through fiber-optic cable 10 is attenuated by sensor matt 12 to differing degrees as the patient moves on the matt. The light intensity is detected by receiver 24 (FIG. 1), amplified, and converted to digital by ADC 28. The light intensity can be measured and converted to digital values that have arbitrary units (AU).

The raw data when plotted over time in FIG. 8 show two major peaks that correspond to peaks in the slower breathing cycle. There are also several minor peaks that generally correspond to peaks in the faster heart beat cycle. The heart rate appears to be about 5 times the respiration rate in this raw data. However, extracting the heart rate from the raw data is more difficult because the smaller heart movements are superimposed on the larger and slower respiration movements.

FIG. 9 shows a prior-art BCG waveform of a single heart beat. An Electro CardioGram (ECG) is measured by electrodes on a patient's chest that measure small electrical currents caused by the patient's heart contracting. A Ballisto CardioGram (BCG) is based on the heart's physical movement. The human heartbeat as measured by a BCG tends to have the shape shown in FIG. 5, where the wave peaks and valleys get progressively larger in amplitude until the largest wave known as the J peak, after which the wave peaks and valleys have decreasing amplitudes.

The H peak and I valley precede the J peak, while the K, L, M, and N valleys and peaks follow the J wave. These tend to be the largest amplitude peaks and valley of the human BCG heartbeat.

The BCG waveform is similar to the Daubechies dB5 wavelet function, so the inventors use dB5 wavelets to analyze BCG waveforms. Daubechies wavelets can have differing numbers of vanishing points and taps. The dB5 wavelet has 5 vanishing points and is the best match of Daubechies wavelets with the BCG waveform, so the inventors use dB5 rather than dB4, dB6, or other Daubechies wavelets.

FIG. 10 shows the prior-art Daubechies dB5 wavelet function. This wavelet function has the same general shape as the BCG waveform of the human heartbeat, so data scientists sometimes use this function for data analysis of BCG waveforms. The maximum of the dB5 wavelet function corresponds to the J peak of the BCG, with the smaller initial peak corresponding to the H peak and the large valley before the main peak corresponding to the I valley of the BCG. After the primary peak of the dB5 wavelet function, a large valley corresponds to the K valley, followed by another peak that corresponds to the L peak of the BCG, with a smaller M valley and a small N peak also seen to correspond between the BCG and dB5 wavelet function.

FIG. 11 shows the prior-art Daubechies dB5 scaling function. The Daubechies dB5 wavelet function is paired with the Daubechies dB5 scaling function. The dB5 scaling function has successively smaller peaks and valleys, in contrast to the dB5 wavelet function. Both functions are useful for wavelet decomposition and reconstruction.

Figure 12:
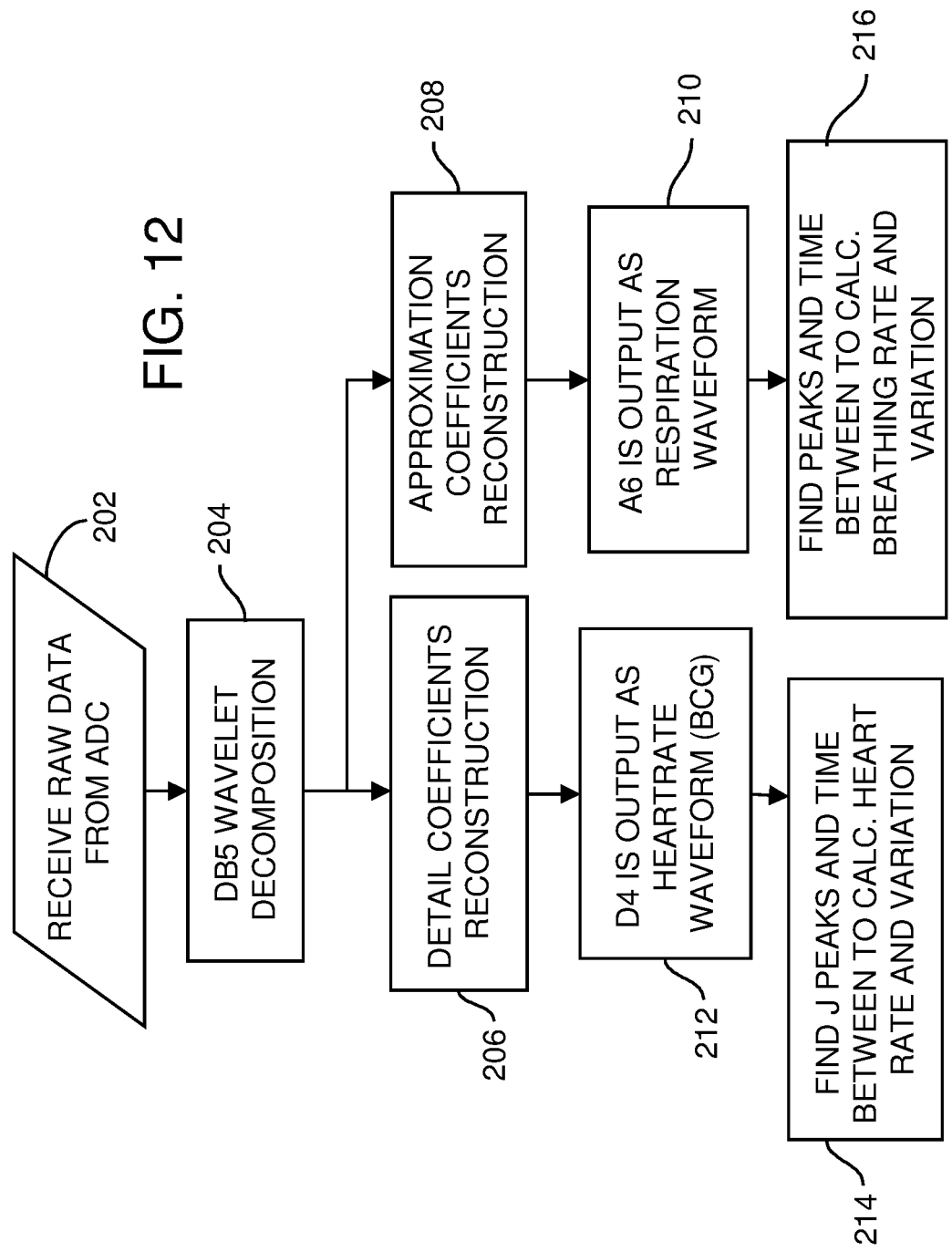
FIG. 12 is a flowchart of an integrated procedure to extract both respiration and heart rates from raw optical-fiber data.

FIG. 12 is a flowchart of an integrated procedure to extract both respiration and heart rates from raw optical-fiber data. The heart rate waveform obtained from the fiber-optic matt is a BallistoCardioGram (BCG) since it is based on the heart's movement rather than electrical pulses from the heart, as in an ECG.

The raw data over a time period is obtained from the ADC for the light attenuation through the sensor matt, step 202. The dB5 wavelet function is used to decompose the raw data, step 204. This decomposition proceeds over several levels by successively using the dB5 scaling function to calculate a waveform for each new level, and using the dB5 wavelet function at each level to decompose that level's waveform.

The detail coefficients for each level are the coefficients obtained by the dB5 wavelet function operating upon that level's waveform. These detail coefficients are used to reconstruct waveforms for the selected level 4, step 206.

The approximation coefficients for each level are the coefficients obtained by the dB5 scaling function operating upon that level's waveform to generate the waveform for the next level. The approximation coefficients (cA6) at level 6 are used to reconstruct the approximation waveform from level 6, step 208. This level 6 reconstructed waveform, A6, is output as the respiration-rate waveform, step 210.

This A6 waveform is analyzed to find the major peaks, which are assumed to correspond to the peaks for the respiration waveform, and the time between these major peaks is used to determine the respiration rate, step 216. If desired, the variation in these peak-to-peak times can be used to determine the variation in respiration rate, such as the standard deviation of the respiration rate.

The detail coefficients at level 4, cD4, are used to reconstruct the waveform for level 4, D4. This level 4 reconstructed waveform, D4, is output as the heart-rate BCG waveform, step 212. This D4 waveform is analyzed to find the major peaks, which are assumed to correspond to the J peaks for the BCG waveform, and the time between these major (J) peaks is used to determine the heart rate, step 214. If desired, the variation in these peak-to-peak times can be used to determine the variation in heart rate, such as the standard deviation of the heart rate.

The relatively complex dB5 wavelet decomposition process, step 204, is used for extracting both respiration and heart rates. Thus both heart rate BCG and respiration rate waveforms are obtained from the same process. Using the same process for both heart rate and respiration rate significantly reduces the complexity and cost of the fiber-optic sensor system.

FIG. 13 is a diagram illustrating an integrated Daubechies wavelet process to reconstruct both respiration and BCG waveforms. This overall process is a Fast Wavelet Transform (FWT) process.

The dB5 wavelet function (See FIG. 10) is shown as function H[N], and is sometimes referred to as the high-pass decomposition filter since it generates detail coefficients cD1-cD4. The inverse transform of this function is H1[N], the high-pass reconstruction filter.

The dB5 scaling function (See FIG. 11) is shown as function G[N], and is sometimes referred to as the low-pass decomposition filter since it generates approximation coefficients cA1-cA6. The inverse transform of this function is G1[N], the low-pass reconstruction filter.

The raw data from the sensor, X[N], is convoluted with the dB5 wavelet function H[N] (See FIG. 10) and down-sampled to generate the deconstructed level-1 detail coefficients cD1. The reconstructed level-1 waveform D1 can be obtained by convoluting these coefficients cD1 with the inverse reconstruction filter H1[N] from the dB5 wavelet function followed by up-sampling.

The raw data X[N] is also convoluted with the dB5 scalar function G[N] and then downsampling to generate cA1, the level-1 approximation coefficients. These level-1 approximation coefficients cA1 can be convoluted with the dB5 wavelet function H[N] and down-sampled to generate the deconstructed level-2 detail coefficients cD2. The reconstructed level-2 waveform D2 could be obtained convoluting these coefficients cD2 with the inverse reconstruction filter H1[N] from the dB5 wavelet function followed by up-sampling.

The level 2 approximation coefficients cA2 are obtained from the level 1 approximation coefficients cA1 by convoluting with the dB5 scalar function G[N] and then downsampling to generate cA2, the level-2 approximation coefficients. These level-2 approximation coefficients cA2 can be convoluted with the dB5 wavelet function H[N] and down-sampled to generate the deconstructed level-3 detail coefficients cD3. The reconstructed level-3 waveform D3 could be obtained by convoluting these coefficients cD3 with the inverse reconstruction filter H1[N] from the dB5 wavelet function followed by up-sampling.

The level 3 approximation coefficients cA3 are obtained from the level 2 approximation coefficients cA2 by convoluting with the dB5 scalar function G[N] and then downsampling to generate cA3, the level-3 approximation coefficients. These level-3 approximation coefficients cA3 can be convoluted with the dB5 wavelet function H[N] and down-sampled to generate the deconstructed level-4 detail coefficients cD4. The reconstructed level-4 waveform D4 is obtained by convoluting these coefficients cD4 with the inverse reconstruction filter H1[N] from the dB5 wavelet function followed by up-sampling.

The reconstructed level-4 D4 waveform is output as the BCG waveform.

The level 4 approximation coefficients cA4 are obtained from the level 3 approximation coefficients cA3 by convoluting with the dB5 scalar function G[N] and then downsampling to generate cA4. The level 5 approximation coefficients cA5 are obtained from the level 4 approximation coefficients cA4 by convoluting with the dB5 scalar function G[N] and then downsampling to generate cA5, the level-5 approximation coefficients.

Finally, these level-5 approximation coefficients are convoluted with the dB5 scalar function G[N] and then downsampling to generate cA6. These level-6 approximation coefficients cA6 are upsampled and convoluted with the inverse reconstruction filter G1[N] from the dB5 wavelet function to obtain the reconstructed level-6 approximation waveform, A6. The reconstructed level-6 D6 waveform is output as the extracted respiration waveform.

FIG. 14 shows reconstructed detail waveforms generated by the integrated FWT process of FIG. 13. The level-1 to level-5 waveforms D1 to D5 are shown, having been reconstructed from the same raw data X[N]. In general, higher levels have smoother data because the dB5 scaling function has been successively applied to generate the approximation coefficients that are input to each level in the FWT process of FIG. 13. Successively applying the dB5 scaling function has the effect of successively smoothing the data input to each successive level.

The level-4 waveform, D4, is selected and output as the BCG waveform. This D4 waveform was extracted from the raw data by successively convoluting the raw data with the dB5 scaling function to reach the level 4 approximation coefficients, and then convoluting with the dB5 wavelet function and downscaling to obtain the level-4 detail coefficients, and finally upsampling and inverse transforming to obtain the D4 waveform.

FIG. 14 shows that the D4 waveform resembles a human heartbeat more than the other earlier-level waveforms D1, D2, D3. The next level waveform, D5, has received too much smoothing, so that the heart beat signal is diminished too much. Visually, D4 is a better match to the human heartbeat BCG of FIG. 9 than D5 or D1-D3. Thus the inventors select D4 from level 4 for outputting the BCG waveform.

FIG. 15 shows reconstructed approximation waveforms generated by the integrated FWT process of FIG. 13. The level-1 to level-6 waveforms A1 to A6 are shown, having been reconstructed from the same raw data X[N]. Although only the reconstruction for level-6 (A6) was shown in FIG. 13, a similar reconstruction could be made for other levels 1 to 5 to obtain waveforms A1 to A5. This reconstruction of A1 to A5 is not needed by the actual sensor system, but is only used here for illustration and comparison to better understand the process and choices.

In general, higher levels have smoother data because the dB5 scaling function has been successively applied to generate the approximation coefficients that are input to each level in the FWT process of FIG. 13. Successively applying the dB5 scaling function has the effect of successively smoothing the data input to each successive level.

The level-6 waveform, A6 is selected and output as the respiration waveform. The slower respiration rate is better matched by a higher level (level 6) waveform than the faster heart rate (level 4, D4, FIG. 15). The slower respiration rate is more easily extracted from a smoother waveform.

Figure 16A:
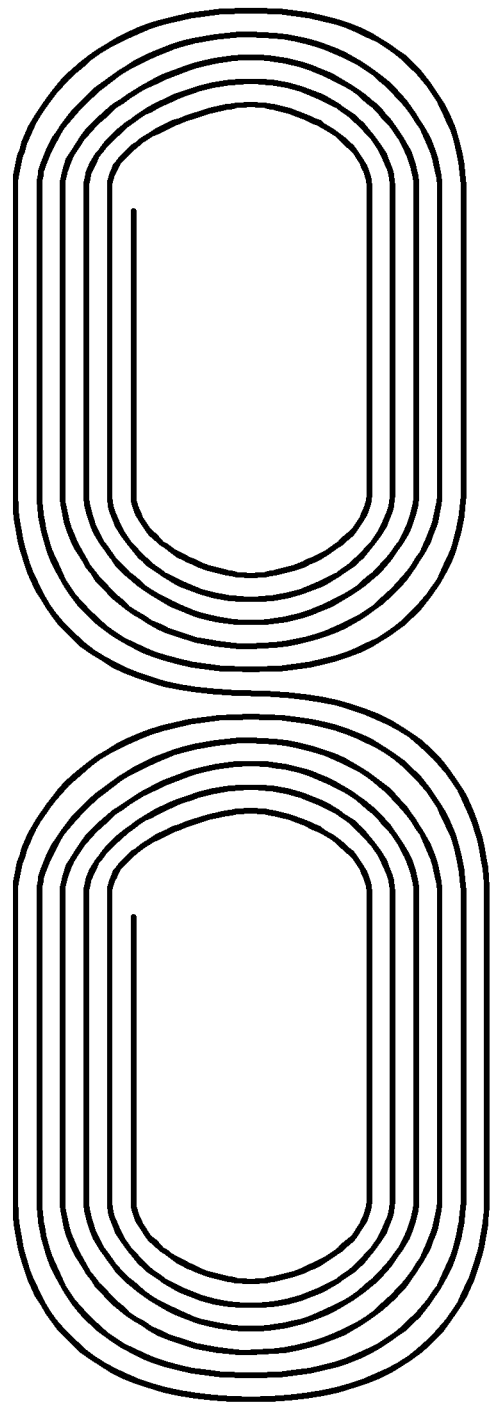
FIGS. 16A-16D show alternative arrangements of the symmetric pair of radial ring groups of the fiber-optic cable.

FIGS. 16A-16D show alternative arrangements of the symmetric pair of radial ring groups of the fiber-optic cable. In FIG. 16A, the symmetric pair of radial ring groups each have endpoints in their centers that face in the same direction, to the right. The groups are connected together by the outer rings of the fiber-optic cable, that connects from the upper-left of the right group to the lower-right of the left group. Since both group's endpoints face in the same direction, the fiber-optic cable can be connected or extended to lead and exit portions easily.

Figure 16B:
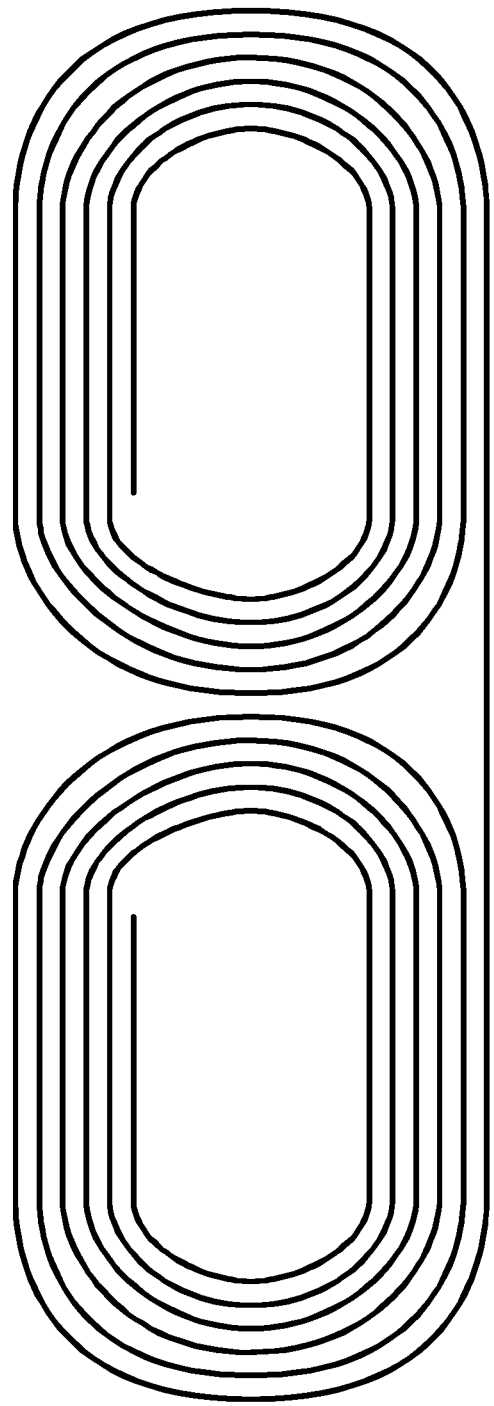

In FIG. 16B, the symmetric pair of radial ring groups are mirror images of each other. Each group has an endpoint in their centers that face toward each other, toward the middle of the matt. The groups are connected together by the outer rings of the fiber-optic cable, that connect from the lower-left of the right group to the lower-right of the left group.

Figure 16C:
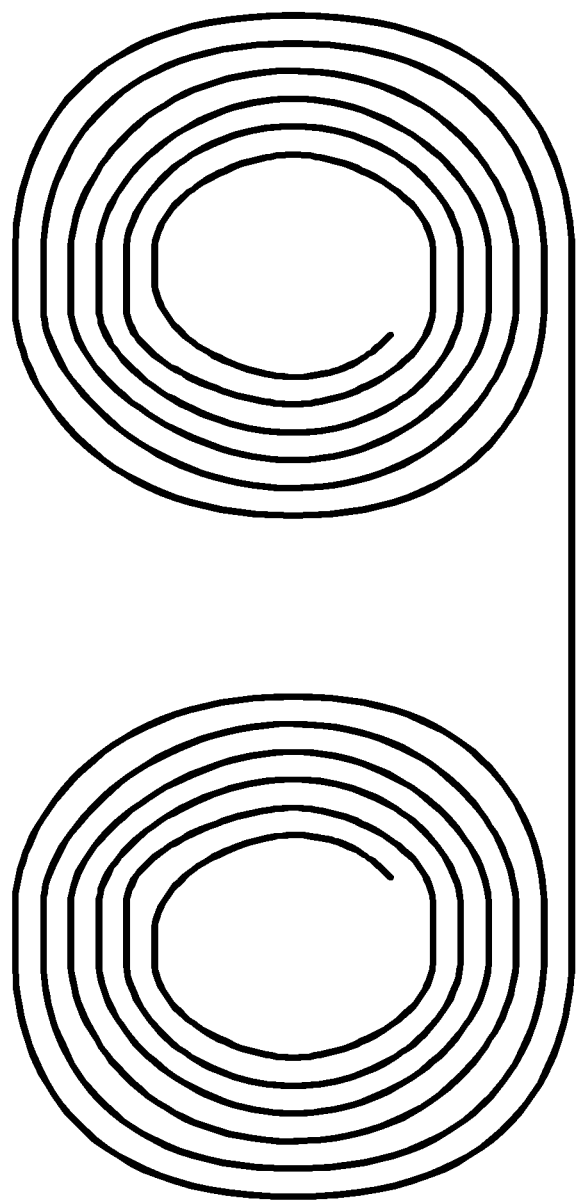
Figure 16D:
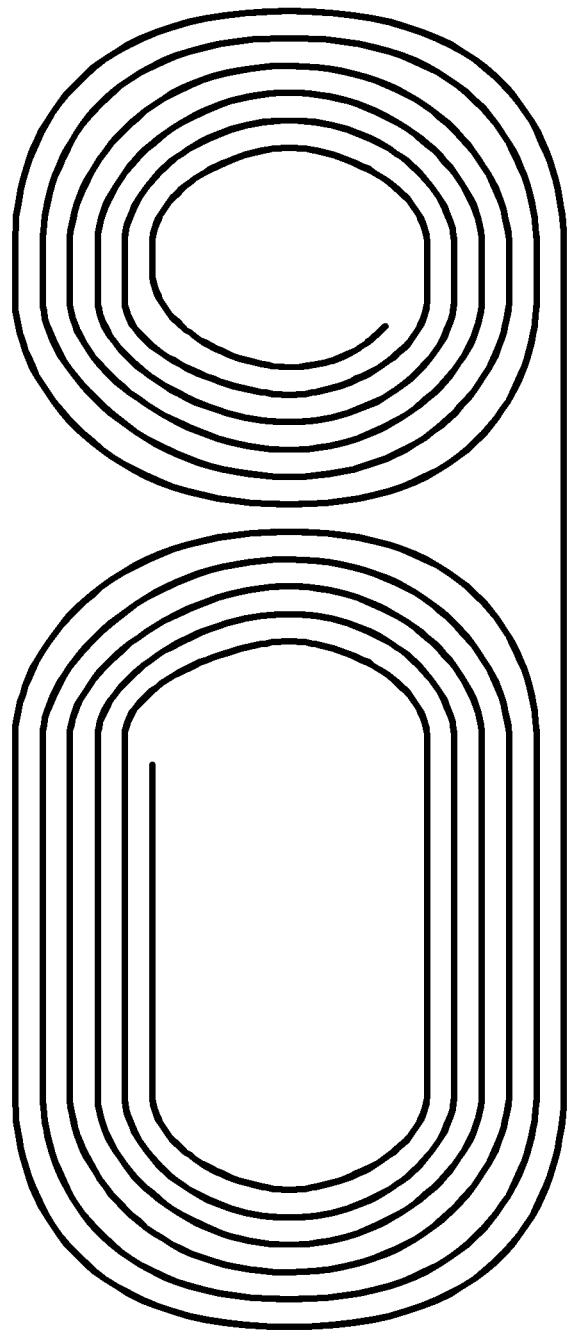

In FIG. 16C, the symmetric pair of radial ring groups are circular rather than oval-shaped. In FIG. 16D, the right radial ring group is circular while the left group is oval-shaped. The pitch and spacing between adjacent rings is constant within the symmetric pair of radial ring groups, providing a uniform stress distribution for each contact point with the person. This uniform stress distribution provides for better reading sensitivity.

ALTERNATE EMBODIMENTS

Several other embodiments are contemplated by the inventors. For example, current driver 22 can control the power level of LED 20 by regulating the current. The overall peak current may be regulated, or the LED may be pulsed on and off, and the on time regulated. LED 20 could be replaced by a high-power laser, a focused laser, a 1550 nm laser, or another more-expensive light source, although using an inexpensive LED can result in a lower-cost product.

The leader and exit portions of fiber-optic cable 10 that exit the plane of the symmetric pair of radial ring groups can be inserted between mesh 18 and bottom layer 16. Having mesh 18 between the leader and exit portions of fiber-optic cable 10 and the symmetric pair of radial ring groups can provide extra padding at fiber cross-overs to prevent wear of the fiber optic cable or uneven pressure and irregular readings.

While the sensor matt with the symmetric pair of radial ring groups has application to extracting BCG and respiration waveforms for a human patient, the sensor matt could be used to detect analyze other micro-movements, such as in an industrial plant, a laboratory, a security system, an engine monitor, or in other environments and applications. Other levels of the reconstructed detail and approximation waveforms could be selected based on the application.

The FWT method can also be useful for reducing noise from other sources, such as vibrations from motors and other nearby equipment. Additional process steps may be added, and some steps may be re-ordered or operated in parallel with other steps.

The sensor system may be periodically re-calibrated, such as by determining an average reading or light intensity over time, and then adjusting current driver 22 to adjust the light intensity from LED 20 to move this average reading toward a mid point or other set point within the range of receiver 24. The high-to-low range of ADC 28 could also be adjusted to better fit the received data, or the received signals could be scaled, such as by adjusting the amplification factor of amplifier 26. Recalibrations could be performed periodically, such as every hour or every minute, or when power-up occurs.

While one pair of radial rings has been shown in FIGS. 1, 2, 6, and 16A-D, and additional pairs of rings are not necessary, fiber-optic cable 10 may be arranged into many pairs of rings. The number of rings within each group of the symmetric pair of radial ring groups can vary. A large ring could be paired with a smaller ring. The circular shape of the rings allows for any alignment to the mesh when the mesh is symmetric. Non-symmetric meshes could also be used but there may be measurement noise from misalignments. The distance between the two ring groups could be small or large, and the two ring groups do not have to be side-by-side, but could be diagonal to each other or have some other placement. The overall size of the sensor matt could be as large as a regular sleeping mattress, or could be smaller. Much smaller sensor matts could be used for chairs or seats to sense respiration and BCG of a person who is sitting rather than laying down.

The extracted respiration waveform could be further analyzed to detect breathing abnormalities, such as halted breather, shallow breathing, coughing, sneezing, etc. Another one of the reconstructed approximation waveforms generated by the integrated FWT process could be used rather than A6. Likewise, the extracted BCG waveform could be further analyzed to detect abnormal heart rhythms, such as bradycardia, high heart rates, skipped beats, atrial fibrillation, etc.

While mesh 18 has been shown as having rectangular openings, other opening shapes are possible, such as circles, ovals, other polygons, slats, etc. The openings could all be uniform size and shape, or they could vary. Mesh 18 could be constructed from a flat sheet of material with openings cut out or punched out, rather than from strands intertwined together as shown in FIG. 5. There may be additional layers in sensor matt 12, or mesh 18 may be integrated with bottom cover 12. In particular, additional padding or support material may be placed on top cover 14 where fiber-optic cable 10 enters and exits the plane of the symmetric pair of radial ring groups to connect to the leader and exit portions of fiber-optic cable 10.

In various embodiments of the disclosed optical fiber sensor, the mesh layer of the deformer is configured such that the open area between fibers is between 30% and 60% of the total mesh surface area. In some embodiments, the through-holes of the mesh layer are sized to receive an entire diameter of the optical fiber (~250 μm). In some embodiments, the through-holes of the mesh layer are sized to receive the width of an optical fiber structure, including the optical fiber and surrounding outer coating. Thus, in some embodiments, the opening of the mesh layer is 100% to 300% of the total diameter of the optical fiber. In some embodiments, the opening of the mesh layer is 130% to 170% of the total diameter of the optical fiber. In other embodiments, the opening W is 250-750 μm, while the diameter D of the mesh fiber is set from 180 to 540 μm. In another embodiment, for an optical fiber with a 100 um core diameter, a 125 um cladding layer diameter, and a 250 um total diameter, the diameter ratio of D to W is selected to around 0.5-0.6.

Directional terms such as up, down, above, below, left, right are relative and depend on the perspective of the viewer. The top layer of the sensor matt could be on top or on the bottom, depending on how the matt is placed.

The raw sensor data can be linear or logarithmic or at some other scale that depends on the non-linearities of the light receiver, amplifier, and ADC. These non-linearities should cancel out when extracting rates such as heart rate or respiration rate.

The background of the invention section may contain background information about the problem or environment of the invention rather than describe prior art by others. Thus inclusion of material in the background section is not an admission of prior art by the Applicant.

Any methods or processes described herein are machine-implemented or computer-implemented and are intended to be performed by machine, computer, or other device and are not intended to be performed solely by humans without such machine assistance. Tangible results generated may include reports or other machine-generated displays on display devices such as computer monitors, projection devices, audio-generating devices, and related media devices, and may include hardcopy printouts that are also machine-generated. Computer control of other machines is another tangible result.

Any advantages and benefits described may not apply to all embodiments of the invention. When the word "means" is recited in a claim element, Applicant intends for the claim element to fall under 35 USC Sect. 112, paragraph 6. Often a label of one or more words precedes the word "means". The word or words preceding the word "means" is a label intended to ease referencing of claim elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word "means" are not intended to fall under 35 USC Sect. 112, paragraph 6. Signals are typically electronic signals, but may be optical signals such as can be carried over a fiber optic line.

The foregoing description of the embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. A fiber-optic sensor comprising:
a fiber-optic cable having an inner core that carries light, a cladding layer around the inner core to reflect light back into the inner core, and an outer coating, wherein a diameter of the inner core is at least 50% of a diameter of the cladding layer around in the inner core;
a symmetric pair of radial ring groups formed by the fiber-optic cable being arranged in a first plane and circled from inside to outside in a first radial ring group in the symmetric pair of radial ring groups, and circled from outside to inside in a secondi radial ring group in the symmetric pair of radial ring groups;
a light source coupled to input an input light into a first end of the fiber-optic cable;
an optical receiver that senses changes in intensity of received light that is received by the optical receiver from a second end of the fiber-optic cable after the input light passes through the symmetric pair of radial ring groups;
a mesh layer having openings formed within the mesh layer, the mesh layer formed in a second plane that is substantially parallel to the first plane;
wherein when pressure is applied by a body, the mesh layer presses upon the fiber-optic cable in the symmetric pair of radial ring groups, wherein a first portion of the fiber-optic cable bends partially into the openings and a second portion of the fiber-optic cable flexes against the mesh layer to vary attenuation of light passing through the fiber-optic cable;
an Analog-of-Digital Converter (ADC) that converts electrical signals from the optical receiver to digital values;
a control and processing unit that processes the digital values from the ADC to generate a respiration rate and a heart rate of the body, wherein the body is moving due to respiration and due to a beating heart within the body;
wherein the control and processing unit performs Daubechies dB5 wavelet decomposition on the digital values;
wherein the control and processing unit performs Daubechies dB5 wavelet decomposition on the digital values to generate intermediate values that include detail coefficients and approximation coefficients;

wherein the control and processing unit performs reconstruction on the detail coefficients to generate a reconstructed dB5 level-4 detail waveform;
wherein the control and processing unit performs reconstruction on the approximation coefficients to generate a reconstructed dB5 level-6 approximation waveform;
wherein the heart rate is extracted from peaks in the reconstructed dB5 level-4 detail waveform;
wherein the respiration rate is extracted from peaks in the reconstructed dB5 level-6 approximation waveform;
wherein the digital values are convoluted with a dB5 scaling function and downsampled to generate a plurality of level-1 approximation coefficients;
wherein the plurality of level-1 approximation coefficients are convoluted with the dB5 scaling function and downsampled to generate a plurality of level-2 approximation coefficients;
wherein the plurality of level-2 approximation coefficients are convoluted with the dB5 scaling function and downsampled to generate a plurality of level-3 approximation coefficients;
wherein the plurality of level-3 approximation coefficients are convoluted with the dB5 scaling function and downsampled to generate a plurality of level-4 approximation coefficients.

2. The fiber-optics sensor of claim 1 wherein the plurality of level-3 approximation coefficients are convoluted with a dB5 wavelet function and downsampled to generate a plurality of level-4 detail coefficients;
wherein the plurality of level-4 detail coefficients are upsampled and transformed with an inverse transform of the dB5 wavelet function to generate the reconstructed dB5 level-4 detail waveform that the heart rate is extracted from.

3. The fiber-optics sensor of claim 2 wherein the reconstructed dB5 level-4 detail waveform is output as a BallistoCardioGram (BCG).

4. The fiber-optics sensor of claim 2 wherein the plurality of level-4 approximation coefficients are convoluted with the dB5 scaling function and downsampled to generate a plurality of level-5 approximation coefficients;
wherein the plurality of level-5 approximation coefficients are convoluted with the dB5 wavelet function and downsampled to generate a plurality of level-6 approximation coefficients;
wherein the plurality of level-6 approximation coefficients are upsampled and transformed with an inverse of the dB5 scaling function to generate the reconstructed dB5 level-6 approximation waveform that the respiration rate is extracted from.

5. The fiber-optics sensor of claim 1 wherein a surface area of the openings in the mesh layer is between 30% and 60% of a total surface area of the mesh layer that includes the openings.

6. The fiber-optics sensor of claim 5 wherein light passing through the fiber-optic cable is attenuated by microbending of the fiber-optic cable.

7. The fiber-optics sensor of claim 6 wherein no crossover of the fiber-optic cable occurs within the symmetric pair of radial ring groups.

8. The fiber-optics sensor of claim 6 wherein the light source is a non-coherent light source.

9. The fiber-optics sensor of claim 8 wherein the non-coherent light source is a Light-Emitting Diode (LED).

10. The fiber-optics sensor of claim 6 further comprising:
a power regulator to the light source, the power regulator for adjusting a power level of the light source to adjust an intensity of the input light into a first end of the fiber-optic cable.

11. The fiber-optics sensor of claim 6 wherein the symmetric pair of radial ring groups comprise circular-shaped ring groups.

12. The fiber-optics sensor of claim 6 wherein the symmetric pair of radial ring groups comprise oval-shaped ring groups.

13. The fiber-optics sensor of claim 6 wherein the symmetric pair of radial ring groups comprise a circular-shaped ring group and an oval-shaped ring group that are connected together at an outer ring in the symmetric pair of radial ring groups.

14. A dual-vital-sign monitor comprising:
a sensor matt having a mesh layer, a fiber-optic cable arranged in a coil pattern, and a top cover layer that presses the fiber-optic cable into the mesh layer to bend the fiber-optic cable to modulate light in the fiber-optic cable;
a light source that generates a light into a first end of the fiber-optic cable;
a light sensor that generates a sensor output that indicates an intensity of light received by the light sensor from a second end of the fiber-optic cable after the light is modulated by the sensor matt;
an Analog-to-Digital Converter (ADC) that converts the sensor output to digital intensity values; and
a processing unit that performs a Daubechies dB wavelet and scaling function convolution with the digital intensity values;
the processing unit also generating a BallistoCardioGram (BCG) waveform by reconstructing a level 4 detail waveform from level 4 detail coefficients generated by the Daubechies dB wavelet and scaling function convolution with the digital intensity values;
the processing unit also generating a respiration waveform by reconstructing a level 6 approximation waveform from level 6 approximation coefficients that are also generated by the Daubechies dB wavelet and scaling function convolution with the digital intensity values;
wherein the processing unit performs Daubechies dB5 wavelet decomposition on the digital intensity values to generate intermediate values that include detail coefficients and approximation coefficients;
wherein the processing unit performs reconstruction on the detail coefficients to generate a reinstructed dB5 level-4 detail waveform;
wherein the processing unit performs reconstruction on the approximation coefficients to generate a reconstructed dB5 level-6 approximation waveform;
wherein the heart rate is extracted from peaks in the reconstructed dB5 level-4 detail waveform;
wherein the respiration rate is extracted from peaks in the reconstructed dB5 level-6 approximation waveform;
wherein the digital intensity values are convoluted with a dB5 scaling function and downsampled to generate a plurality of level-1 approximation coefficient;
wherein the plurality of level-2 approximation coefficients are convoluted with the dB5 scaling function and downsampled to generate a plurality of level-2 approximation coefficients;

wherein the plurality of level-2 approximation coefficients are convoluted with the dB5 scaling function and downsampled to generate a plurality of level-3 approximation coefficients;

wherein the plurality of level-3 approximation coefficients are convoluted with the dB5 scaling function and downsampled to generate a plurality of level-4 approximation coefficients;

whereby both the respiration waveform and the BCG waveform are generated through the Daubechies dB5 wavelet and scaling function convolution on the digital intensity values that are modulated by the sensor matt.

15. The dual-vital-sign monitor of claim 14 wherein the coil pattern of the fiber-optic cable in the sensor matt comprises a symmetric pair of radial ring groups in a substantially planar arrangement when no pressure is placed on the sensor matt.

16. A periodic micro-movement detector comprising:
a fiber-optic cable having an inner core that carries light, a cladding layer around the inner core to reflect light back into the inner core, and an outer coating, wherein a diameter of the inner core is at least 50% of a diameter of the cladding layer around in the inner core;
a sensor matt having a planar mesh layer and the fiber-optic cable arranged in a planar pattern on the planar mesh layer and circled from inside to outside in a first radial ring group in a pair of radial ring groups, and circled from outside to inside in a second radial ring group in the pair of radial ring groups;
a light source coupled to drive an input light into a first end of the fiber-optic cable;
an optical receiver that senses changes in intensity of received light that is received by the optical receiver from a second end of the fiber-optic cable after the input light passes through the pair of radial ring groups;
a plurality of openings in the planar mesh layer;
wherein when pressure is applied by a moving body, the planar mesh layer presses upon the fiber-optic cable in the pair of radial ring groups, wherein a first portion of the fiber-optic cable bends partially into the plurality of openings and a second portion of the fiber-optic cable flexes against the planar mesh layer to vary attenuation of light passing through the fiber-optic cable;
an Analog-to-Digital Converter (ADC) that converts electrical signals from the optical receiver to digital values; and a processing unit that performs Daubechies dB5 wavelet decomposition on the digital values to generate intermediate values that include detail coefficients and approximation coefficients;

wherein the processing unit performs reconstruction on the detail coefficients to generate a reconstructed dB5 level-4 detail waveform;

wherein the processing unit performs reconstruction on the approximation coefficients to generate a reconstructed dB5 level-6 approximation waveform;

wherein a heart rate is extracted from peaks in the reconstructed dB5 level-4 detail waveform;

wherein a respiration rate is extracted from peaks in the reconstructed dB5 level-6 approximation waveform;

wherein the processing unit performs Daubechies dB5 wavelet decomposition on the digital values to generate intermediate value that include detail coefficients and approximation coefficients;

wherein the processing unit performs reconstruction on the detail coefficients to generate the reconstructed dB5 level-4 detail waveform;

wherein the processing unit preforms reconstruction on the approximation coefficients to generate the reconstructed dB5 level-6 approximation waveform;

wherein the heart rate is extracted from peaks in the reconstructed dB5 level-4 detail waveform;

wherein the respiration rate is extracted from peaks in the reconstructed dB5 level-6 approximation wavefront;

wherein the digital values are convoluted with a dB5 scaling function and downsampled to generate a plurality of level-1 approximation coefficients;

wherein the plurality of level-1 approximation coefficients are convoluted with the dB5 scaling function and downsampled to generate a plurality of level-2 approximation coefficients;

wherein the plurality of level-2 approximation coefficients are convoluted with the dB5 scaling function and downsampled to generate a plurality of level-3 approximation coefficients;

wherein the plurality of level-3 approximation coefficients are convoluted with the dB5 scaling function and downsampled to generate a plurality of level-4 approximation coefficients.

* * * * *